United States Patent
Goossen et al.

(10) Patent No.: US 9,532,752 B2
(45) Date of Patent: Jan. 3, 2017

(54) IMAGE-BASED DETERMINATION OF COMPRESSION ELEMENT DEFLECTION

(75) Inventors: Andre Goossen, Radbruch (DE); Harald Sepp Heese, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 238 days.

(21) Appl. No.: 14/342,190

(22) PCT Filed: Aug. 31, 2012

(86) PCT No.: PCT/IB2012/054486
§ 371 (c)(1),
(2), (4) Date: Feb. 28, 2014

(87) PCT Pub. No.: WO2013/035023
PCT Pub. Date: Mar. 14, 2013

(65) Prior Publication Data
US 2014/0226786 A1   Aug. 14, 2014

Related U.S. Application Data

(60) Provisional application No. 61/531,677, filed on Sep. 7, 2011.

(51) Int. Cl.
*A61B 6/04* (2006.01)
*A61B 6/00* (2006.01)
*A61B 6/02* (2006.01)

(52) U.S. Cl.
CPC ............ *A61B 6/0414* (2013.01); *A61B 6/502* (2013.01); *A61B 6/025* (2013.01); *A61B 6/0492* (2013.01); *A61B 6/5217* (2013.01)

(58) Field of Classification Search
CPC ...... A61B 6/0492; A61B 6/503; A61B 6/0414; A61B 6/502
See application file for complete search history.

(56) References Cited

U.S. PATENT DOCUMENTS

2005/0008117 A1* 1/2005 Livingston ............. A61B 6/502
                                                        378/37
2006/0034422 A1* 2/2006 Yang .................... A61B 5/1075
                                                        378/37

(Continued)

FOREIGN PATENT DOCUMENTS

WO    2010102087 A1    9/2010

OTHER PUBLICATIONS

Burch et al: "A Method for Estimating Ecompressed Breast Thickness During Mammography"; The British Journal of Radiology, 1995, vol. 68, pp. 394-399.

(Continued)

*Primary Examiner* — Robert Kim
*Assistant Examiner* — Eliza Osenbaugh-Stewar (57) ABSTRACT

An X-ray imaging system element (3) includes two compression elements (8a, 8b), which are movable relative to one another. An object (10) is introducible and compressible between the compression elements. At least one of the compression elements is adapted to alter its geometrical shape and/or alignment relative to the other during compression. At least one partly X-ray opaque marker element (24) is provided on one of the compression elements, which marker element is adapted to allow detection of an alteration of the geometrical shape of the respective compression element (8a, b).

12 Claims, 7 Drawing Sheets

(56) References Cited

U.S. PATENT DOCUMENTS

| | | | |
|---|---|---|---|
| 2008/0103387 A1* | 5/2008 | Gross | A61B 6/0414 600/424 |
| 2008/0240345 A1 | 10/2008 | Galkin | |
| 2009/0003670 A1 | 1/2009 | Gu et al. | |
| 2009/0076382 A1 | 3/2009 | Shepherd et al. | |
| 2009/0268865 A1* | 10/2009 | Ren | A61B 6/0414 378/37 |

OTHER PUBLICATIONS

Diffey et al: "A Stepwedge-Based Method for Measuring Breast Density: Observer Variability and Comparison With Human Reading"; SPIE, vol. 7622, pp. 76220A-1-76220A-8, 2010.

Malkov et al: "Improvements to Single Energy Absorptiometry Method for Digital Mammography to Quantify Breast Tissue Density"; Digital Mammography Proceedings, LNCS, vol. 5116, pp. 1-8, 2008.

* cited by examiner

IMAGE-BASED DETERMINATION OF COMPRESSION ELEMENT DEFLECTION

CROSS-REFERENCE TO PRIOR APPLICATIONS

This application is the U.S. National Phase application under 35 U.S.C. §371 of International Application No. PCT/IB2012/054486, filed on Aug. 31, 2012, which claims the benefit of U.S. Provisional Patent Application No. 61/531,677, filed on Sep. 7, 2011. These applications are hereby incorporated by reference herein.

FIELD OF THE INVENTION

The invention relates to X-ray imaging technology as well as image post-processing/analysis.

In particular, the present invention relates to image-based determination of a geometrical alteration of the shape of a compression element.

Particularly, the present invention relates to an image-based determination of compression paddle deflection for accurate breast density assessment in mammography applications.

BACKGROUND OF THE INVENTION

Mammography is the modality of choice for screening for early breast cancer. In mammography, preferably low energy X-rays are employed for examining an object, e.g. human breast tissue, as a diagnostic and screening tool. The goal of mammography is the early detection of breast cancer, typically through detection of characteristic masses and/or micro-calcifications.

In this regard, determining breast density is an important indicator for a cancer risk. With the large amount of images generated in mammography screening programs, it is beneficial to have a reliable automatic breast density assessment (BDA) in order to support the user, e.g. a radiologist.

Figure 1:
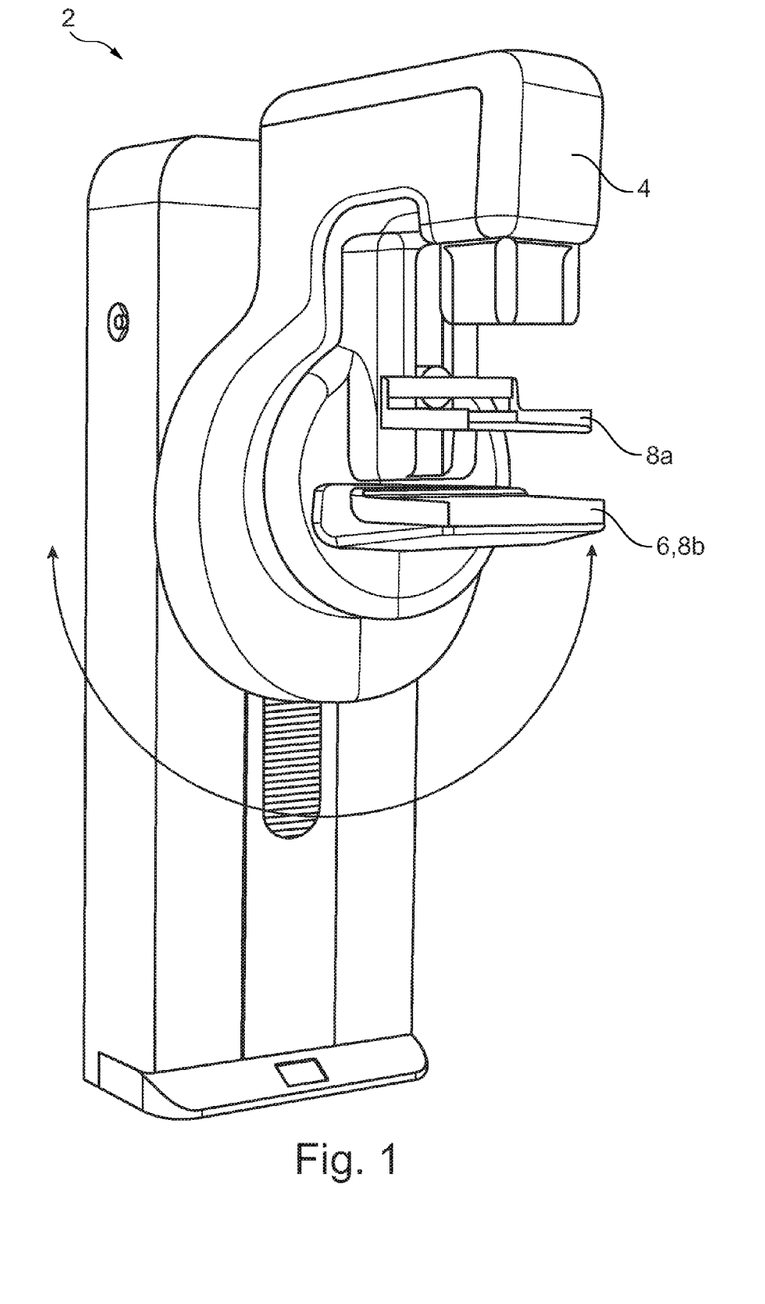
FIG. 1 shows an exemplary embodiment of a mammography system.

FIG. 1 shows an exemplary embodiment of a mammography system. Imaging system 2 comprises X-ray source 4 as well as an X-ray detector 6. X-ray detector 6 also doubles as a second compression element 8b, while a first compression element 8a, e.g. a compression paddle, is arranged between X-ray source 4 and X-ray detector 6. The first and second compression element 8a,b are movable relative to one another, in particular, the first compression element 8a is movable relative to the second compression element 8b/X-ray detector 6.

X-ray source 4 is exemplarily rotatable about an axis for obtaining horizontal/parallel as well as oblique image information. In standard mammography, the surface of the detector 6 is regularly always orthogonal to the line connecting X-ray detector 6 and X-ray source 4. For oblique mammographic views, the entire system 4,6,8 is rotatable, as indicated by the circular arrow in FIG. 1. Angulations of X-ray source 4 with respect to a fixed position of the X-ray detector 6 may be used for tomosynthesis applications.

Figure 2:
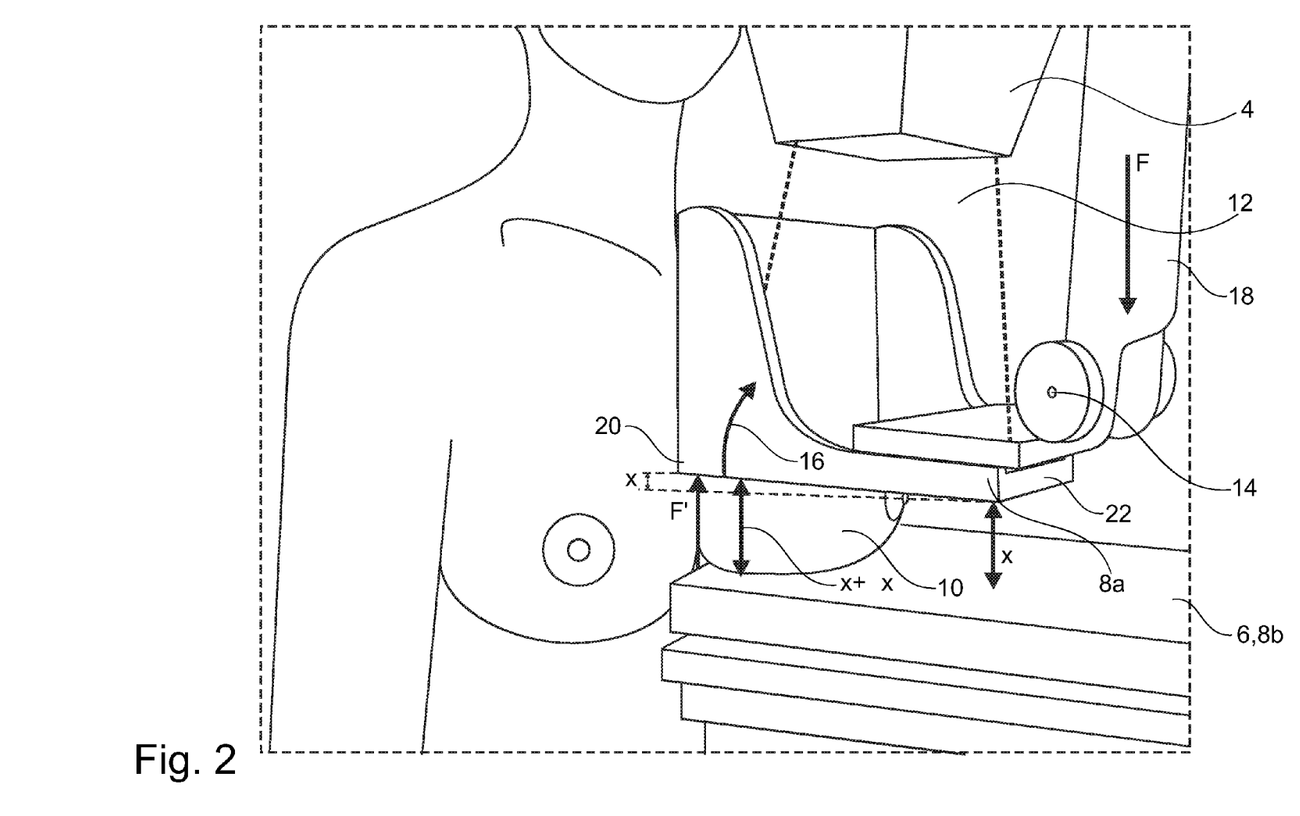
FIG. 2 shows an exemplary mammography screening.

FIG. 2 shows an exemplary mammography screening. An object 10, e.g. human breast tissue, is arranged between the first and second compression elements 8a,b, in particular compressed between the first and second compression elements 8a,b.

The first compression element 8a is attached to a movable arm element 18 allowing a relative movement of the first compression element 8a relative to the second compression element 8b/X-ray detector 6. By moving the first compression element 8a with force F acting in an object distal region 22, object 10 is compressed between the first and second compression element 8a,b. Object 10 is generating a counterforce F' in an object proximal region 20 of the first compression element 8a. Since forces F, F' do not coincide, resulting forces are acting on the first compression element 8a. In particular, a tilt about tilt axis 14 is conceivable as well as, in case the first compression element 8a is not made of an infinite rigid material, a deflection 16 by bending the first compression element 8a. Accordingly, a known distance x between the first and the second compression element 8a,b at the object distal side 22 results in a distance x+Δx at the object proximal side 20 due to counterforce F'.

For determining breast density, precise information about the force F applied to the first compression element 8a as well as the distance x between the first and the second compression element 8a,b is required. Thus, a precise measurement of breast thickness, i.e. distance x, further taking into account additional tilt and deflection of a compression element resulting in Δx is of importance when automatically determining volumetric or mammographic breast density, from image information of digital mammograms. This procedure is also referred to as breast density assessment (BDA). Due to tilt and deflection of a compression element, the actual distance x+Δx may show deviations of Δx=5 mm from the true thickness up to even Δx=15 mm. However, even small errors of 1 to 2 mm may be considered to have a large impact on the breast density assessment, resulting in a significant misjudgement of the density.

SUMMARY OF THE INVENTION

Imprecision in compression thickness measurement may be considered significant for automatic breast density assessment. Such imprecision may result from the height or distance between the first and the second compression element being measured at the far end of the compression elements, i.e. at an object distal region or side, where compression force F is applied, while the height support or object to be examined typically only fills part of the base between the first and the second compression element near the chest wall or at an object proximal region. Additional impreciseness may be introduced by play in the connection of the gantry and paddle or arm and compression element, which may be as large as 15 mm, depending on the system and paddle.

Since even small errors may have a large impact on the estimated breast density, e.g. 1 mm may lead to about 10% misjudgement, not including other effects, e.g. varying compression height caused by paddle deflection or tilt, which cannot be estimated from a single height measurement, it may be beneficial to not only determine distance x between the first and the second compression element but also the resulting shape of a compression element in a compressed state. In other words, in a compressed state, i.e. with an object introduced between the first and second compression element, the geometry of a compression element may be altered, thereby resulting in additional variables, e.g. Δx, which have to be considered for a correct breast density assessment. To increase accuracy, marker elements are provided in one of the first and the second compression element, in particular in or on the first compression element or compression paddle, which may subsequently be detected in acquired X-ray image information and may be evaluated in an image processing step to derive a resulting geometrical shape of the respective compression element to allow determining a precise compression height x+Δx.

Aspects, features and advantages of the present invention may further be derived from the detailed description of preferred embodiments described hereinafter which are explained with reference to the following drawings.

Like elements may be referred to with like reference numerals.

The figures are not drawn to scale, however may depict qualitative proportions.

DETAILED DESCRIPTION OF EMBODIMENTS

To allow a precise breast density assessment, marker elements, e.g. lead marker elements, which may be spherically, circularly or coin-shaped, may be incorporated into one of the compression elements, in particular the compression element, which is expected to be geometrically altered in the compressed state.

The marker elements, in particular X-ray opaque elements or at least partly X-ray opaque elements, may subsequently be detected in the acquired X-ray image information and may be subjected to calculations to determine an occurring misalignment and/or geometrical alteration of the shape of the respective compression element.

E.g., in case only a tilt of the compression element is assumed, three marker elements may be considered to be sufficient for determining the orientation of e.g. a planar compression element, i.e. the orientation of the plane of the compression element with respect to the other compression element.

The X-ray source may be considered to be a point source allowing a precise projection of the respective marker elements onto the X-ray detector and thus into the X-ray image information. In this case, the three marker elements should not be arranged on a single line or marker line but should be arranged so as to unambiguously determine a plane. Since the distance and alignment of the marker elements on the compression element relative to one another is assumed to be known, due to the point source nature of the X-ray source, the precise angulation of the compression element may be determined by known mathematical methods.

In case not only a tilt but also a deflection, bending or warping of the compression element has to be determined, employing only three marker elements spanning a plane may not be sufficient since the distance between the marker elements is not defined any more due to the deflection of the compression element. With small marker elements, e.g. metal spheres or coins, placed on either side of a compression element, it again may be possible to exploit the theorem or intersecting lines for deriving the compression height from the distance of the projected marker positions.

Typically, an image-based detection of the marker elements within the X-ray image information may achieve sub-pixel accuracy, exploiting the detector's point spread function (PSF) as well as focal blur. However, even an accuracy of two pixels would be sufficient for deriving a height with an error smaller than 0.5 mm.

Accordingly, an accuracy of one pixel would lead to below 0.25 mm precision while an accuracy of 4 pixels would be sufficient for a precision smaller than 1 mm. While it may be conceivable to employ the full area of a compression element, it may be beneficial to arrange the marker elements only in that part of the compression element, which would not interfere with a projection of tissue within the X-ray image information. Accordingly, a compression element may comprise an object proximal region as well as an object distal region. In the context of the present invention, the object distal region may be considered that region that would not allow an overlapping of a projected marker and tissue within the X-ray image information.

Placing marker elements along an axis between chest wall and gantry or between the object proximal side and the object distal side, it is conceivable to derive position-specific heights thereby measuring paddle tilt or even deflection. Therefore, marker elements may be arranged in subgroups of at least three marker elements, which are arranged so as to constitute a single line or marker line. Since the distance between the marker elements within a single marker line is assumed to be known, a predefined model, e.g. a linear model or thin-plate-spline model or an interpolation through the measured heights as supporting points may be employed to determine the geometrical shape of the compression element and thus the deflection of the compression paddle.

The true height $x+\Delta x$ on a marker line can be computed via Equation 1:

$$x + \Delta x = h\left(1 - \frac{1}{\left(\frac{1}{1-\frac{x}{h}}\right) + \Delta D[px] \cdot \frac{p}{d}}\right) \quad \text{Equation 1}$$

with:

h: the distance between X-ray source and detector;

$\Delta D[px]$: the measured distance between the actual distance of the marker elements on the detector and the distance for $\Delta x=0$ mm;

p: the pixel size;

d: the distance between marker elements on the compression element;

x: the measured height at the object distal side.

In case of a deflection of the compression element, true height can be computed likewise for several combinations of marker elements resulting in a plurality of supporting points with known true heights, that can be exploited in a thin-plate-spline or polynomial interpolation model.

Using a plurality of marker lines may even allow to determine a two-dimensional bending or warping of the compression element around the object to be determined, i.e. height $x+\Delta x$ is a function of the two-dimensional position on the detector 6. Such a determination may in particular take into account that the deflection or warping of the compression element is required to be a continuous modification of the geometrical shape of the compression element. Exemplary examples for a deviation are provided in the following table, determined by the following equations.

For an exemplary mammography system with a distance between X-ray source and X-ray detector of h=650 mm, a detector area of 239Δ305 mm, d=250 mm, a true object thickness $(x+\Delta x)=50$ mm or measured height x=(50 mm$-\Delta x$) and a detector pixel size of p=0.085 mm, the deviation may be determined as follows. The exemplary marker element distance of d=250 mm exemplifies a case with substantially best accuracy when considering the exemplary dimensions of the detector area.

For these values, the observed marker position difference for a paddle height difference of Δx amounts to $$\Delta D[\text{mm}] = \frac{h}{h-(x+\Delta x)} \cdot d - \frac{h}{h-x} \cdot d \qquad \text{Equation 2}$$

$$= \frac{650 \text{ mm}}{650 \text{ mm} - 50 \text{ mm}} \cdot 250 \text{ mm} -$$

$$\frac{650 \text{ mm}}{650 \text{ mm} - 50 \text{ mm} + \Delta x} \cdot 250 \text{ mm}$$

with ΔD in [mm] or converted to $$\Delta D[px] = \frac{\Delta D[\text{mm}]}{p} = \frac{\Delta D[\text{mm}]}{0.085 \text{ mm}} \qquad \text{Equation 2}$$

with ΔD in detector pixels [px].

Table 1 contains the observed marker distances in the image for a given height difference Δx and thus derives the necessary accuracy to achieve a certain precision of height measurement, e.g. 1.3 pixels marker localization accuracy for 0.25 mm precision in height measurement.

TABLE 1

| deviation Δx[mm] | magnification D[mm] | difference ΔD[mm] | difference ΔD[px] |
|---|---|---|---|
| 0.00 | 270.8 | — | — |
| 1.00 | 270.4 | 0.5 | 5.3 |
| 0.50 | 270.6 | 0.2 | 2.7 |
| 0.25 | 270.7 | 0.1 | 1.3 |
| 0.20 | 270.7 | 0.1 | 1.1 |

Figure 3:
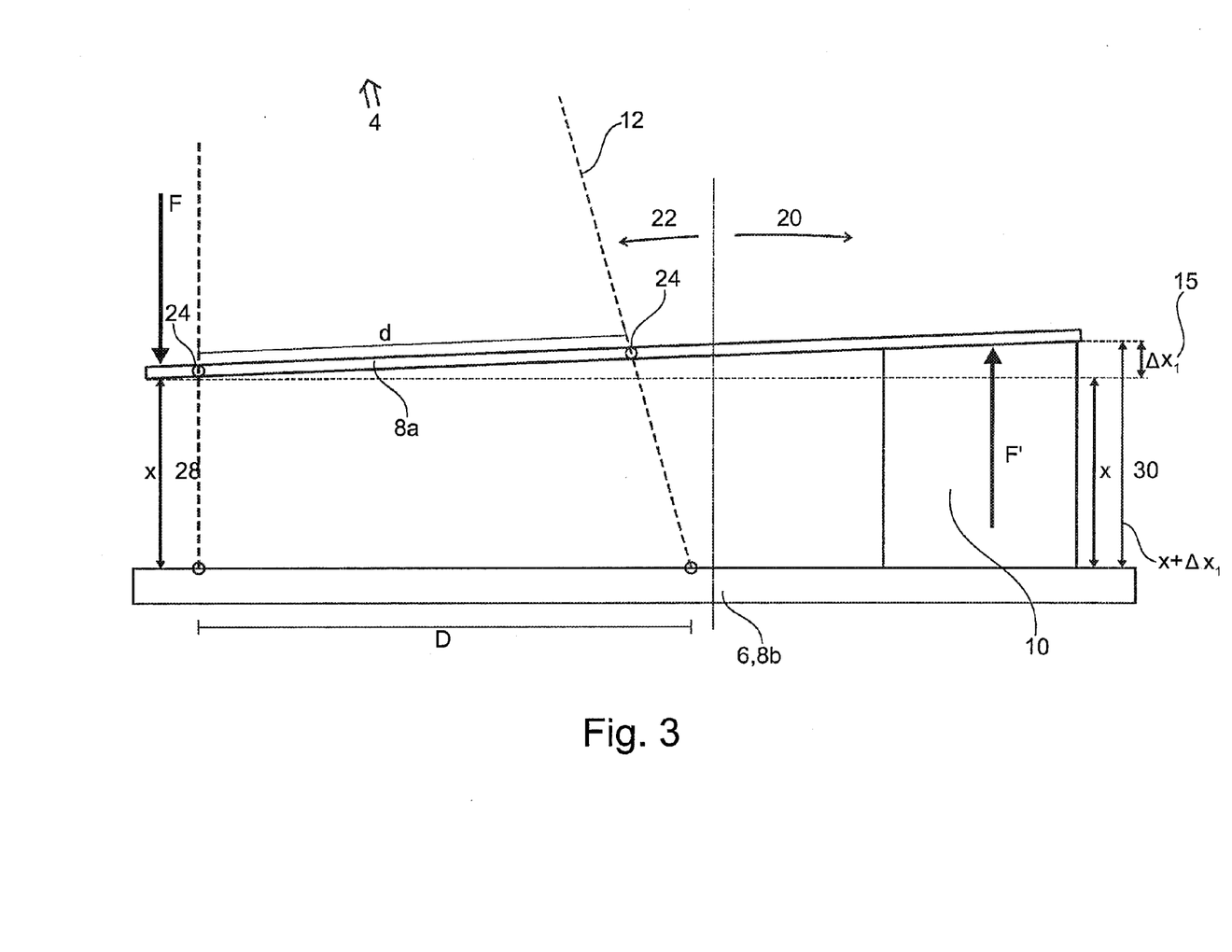
FIGS. 3 to 5 show exemplary embodiments for detecting tilt and/or deflection of a compression element.

FIG. 3 shows an exemplary embodiment of a tilt of a compression element relative to a further compression element.

Exemplarily, a first compression element 8a is tilted relative to a second compression element 8b, e.g. an X-ray detector 6. The first compression element 8a comprises an object proximal region or side 20 and an object distal region or side 22. An arm element or a mounting element for the first compression element 8a, not depicted in FIG. 3, may be assumed at the left side of FIG. 3. On the right side of FIG. 3, an object 10 is arranged between the first and second compression elements 8a,b, e.g. human breast tissue.

The first compression element 8a is forced downwards by force F, depicted at the left side of FIG. 3, while a resistance force F' due to the object 10 being compressed between the first and second compression element 8a,b occurs at the right side. The thickness or distance between the first and second compression elements 8a,b, is regularly measured at the left side, constituting a measured thickness x 28. Due to force F' acting on the right side of FIG. 3, the first compression element 8a is tilted upwards with regard to the second compression element 8b, resulting in a tilt Δx₁ 15.

Accordingly, the actual occurring compression thickness 30 equates to the measured thickness x 28 and the tilt Δx₁. Accordingly, compression thickness 30=x+Δx₁.

In FIG. 3, it is assumed that the first compression element 8a is only tilted with regard to the second compression element 8b without a further geometrical alteration, e.g. a bending or warping of the first compression element. The first compression element 8a comprises exemplarily two marker elements 24, which are arranged in the plane of cross-section of FIG. 3. The distance between marker elements 24 is assumed to be known, thereby allowing, by the projection of the marker elements 24 on the X-ray detector element 6, to reconstruct a tilt angle, thus allowing to determine Δx₁.

By determining the tilt Δx₁ from the projection of the marker elements 24 on detector element 6 by knowing the distance D between the marker elements on compression element 8a and the projected distance D of the marker elements 24 on the X-ray detector 6, the compression thickness 30 may be determined by the measured thickness 28 and Δx₁.

Figure 4:
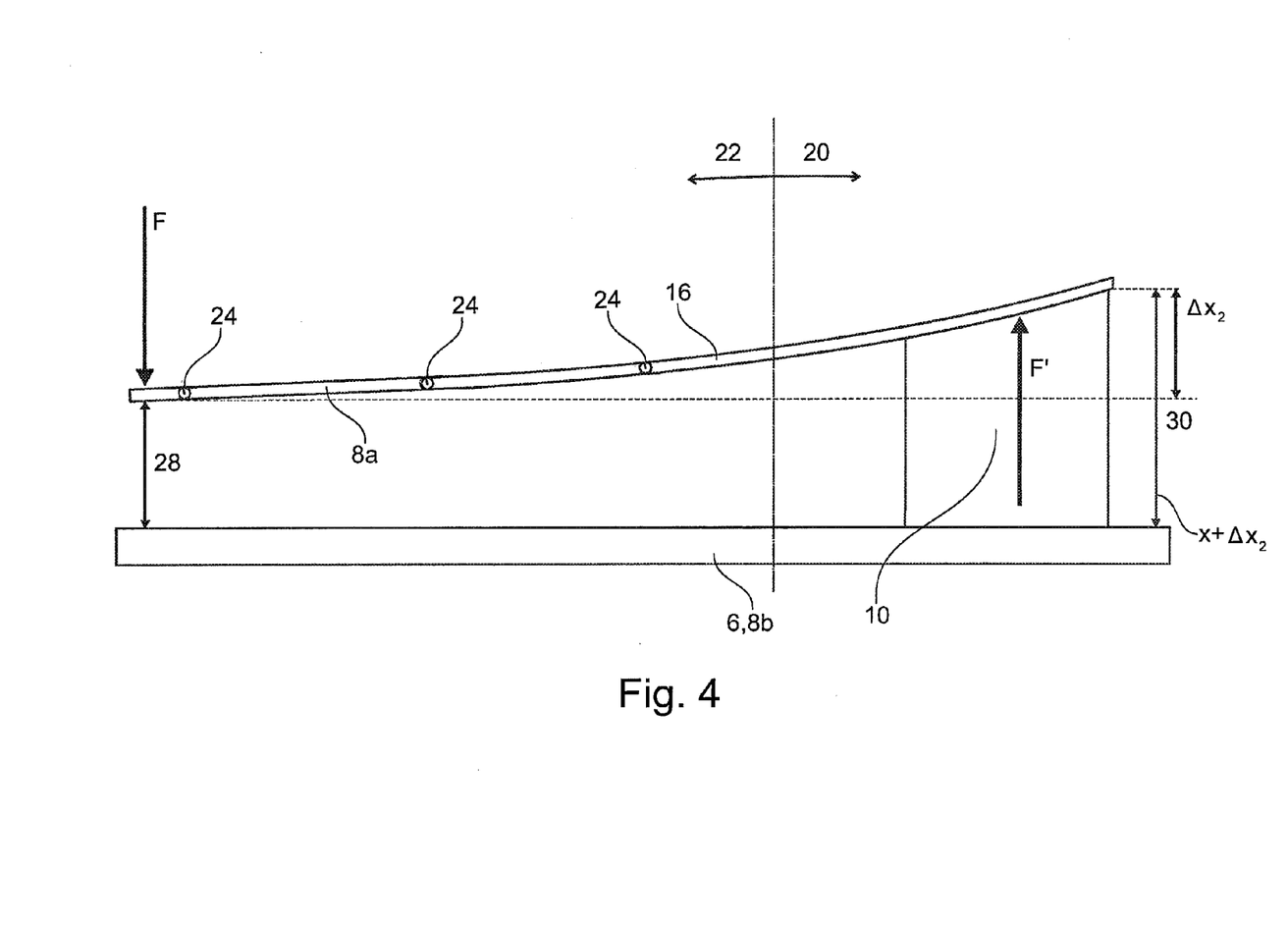

FIG. 4 shows an embodiment where not only a tilt but (also) a deflection or warping of the first compression element occurs. Such a deflection occurs in case the compression element is not made of a stiff, but a to some extent flexible material.

In the plane of the cross-sectional view of FIG. 4, exemplarily three marker elements 24 are arranged. The difference between the measured thickness x 28 and the compression thickness x+Δx₂ 30 is Δx₂, resulting from deflection 16.

Due to the deflection 16 of compression element 8a, the geometrical shape of the compression element is altered as well, an alteration of the distance of the marker elements relative to one another occurs. Since now the distance between the marker elements is not precisely known any more, using only two marker elements would result in an inaccurate determination of Δx₂ and consequently the compression thickness 30. However, by employing at least three marker elements arranged in a single line, a so-called marker line 26, and employing the knowledge that the deformation of the compression element has to be a continuous deformation, said deformation or deflection 16 may be determined and thus Δx₂ may be determined. In this regard, known methods of curvature approximation using known structure support points, i.e. marker elements, the shape of the deflected compression element may be determined with sufficient accuracy to allow determining Δx₂.

Figure 5:
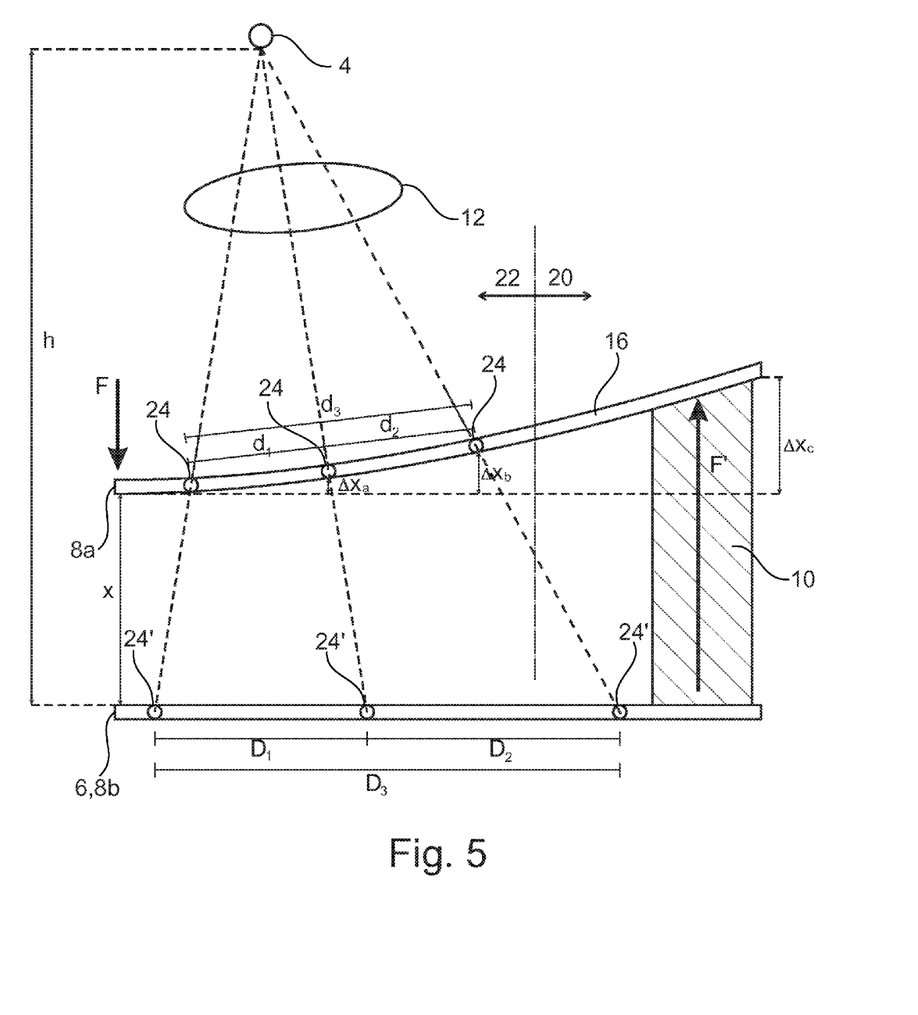

The cross-sectional view of FIG. 4 is further depicted in FIG. 5 in the context of an imaging system 2. X-ray source 4, e.g. embodies as a point source, is generating X-radiation 12 having a cone shape. Exemplarily three marker elements 24 are arranged in a marker line 26 in the plane of cross-section depicted in FIG. 5.

Force F is applied to the object distal side 22, while object 10 is compressed between compression elements 8a,b on the object proximal side 20, thereby generating force F' acting to deflect 16 compression element 8a by Δx. The distance between two adjacent marker elements 24 is indicated as d₁ and d₂, while the distance between the outer marker elements 24 is designated as d₃. X-ray detector 6 obtains projections 24' of marker elements 24 having the respective distances D₁ to D₃.

By knowing the pre-given distances d₁ to d₃, determining projected distances D₁ to D₃ in the image information and employing the assumption that the deformation of the compression element 8a is a continuous deflection 16 caused by a single resulting force F', the shape and alignment of the compression element 8a along the marker line of the three marker elements depicted in FIG. 5 may be determined. In case a completely symmetrical deformation or deflection 16 of compression element 8a is assumed with regard to the plane of cross-section of FIG. 5, using only a single marker line as depicted in FIG. 5 may be considered to be sufficient to determine the overall shape of deflected compression element 8a.

However, in case a non-symmetrical deformation is assumed, a plurality of marker elements or marker lines may be employed to determine the overall three-dimensional shape or deformation of a dedicated compression element. In particular, for each marker element 24, a specific $\Delta x_i$ may be determined, e.g. $\Delta x_{a,b}$, which subsequently allows, by determining the shape of deformed compression element 8a, $\Delta x_c$ at the object proximal side 20 and thus compression height $x+\Delta x_c$.

The sections between two marker elements may either be approximated as a straight line or the bent shape of the compression element may be taken into account by an iterative algorithm.

Figures 6A, 6B:
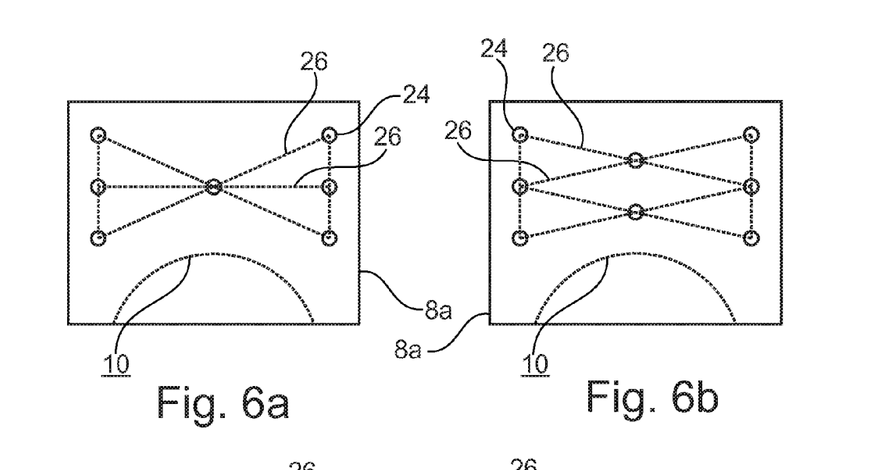
FIGS. 6a-e show exemplary arrangements of marker elements.
Figures 6C, 6D:
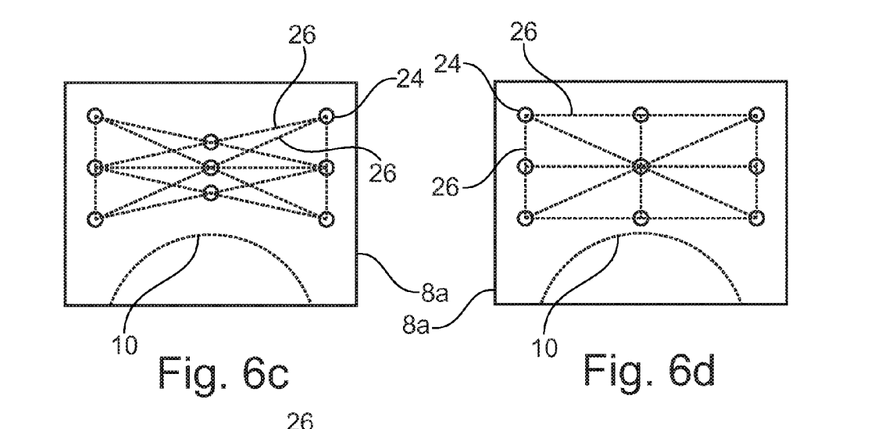
Figure 6E:
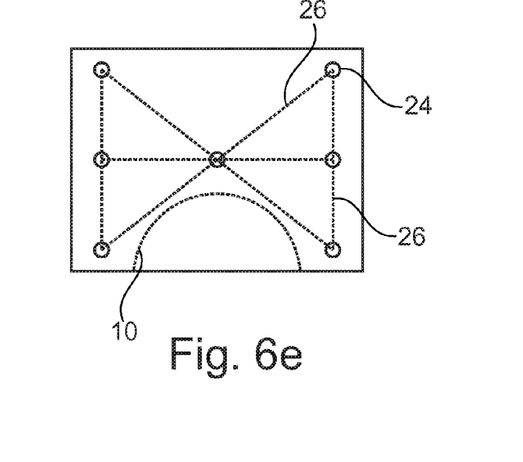

FIGS. 6a-e depict different marker element configurations for determining a three-dimensional alteration of the shape of compression element 8a. The marker elements 24 in FIG. 6a-6d are arranged in an object distal region 22 so not to interfere with projected object information, e.g. by projecting a marker element into the tissue projection of object 10. In FIG. 6e, marker elements 24 are substantially distributed evenly over compression element 8a though still being arranged so as to not interfere with a tissue projection of object 10.

In FIG. 6a, seven marker elements 24 are incorporated into compression element 8a, constituting altogether five marker lines 26, each marker line 26 comprising three marker elements 24.

The accuracy of determining a paddle deflection in the direction of a dedicated marker line may be further increased by employing more than three marker elements 24 within an individual marker line 26, e.g. four, five, six, seven, eight, nine, ten or more marker elements contained in a single marker line. FIG. 6b employs altogether eight marker elements 24 which are arranged so as to constitute six individual, non-identical marker lines 26.

FIGS. 6c and d each comprise nine individual marker elements 24, which however are arranged differently with regard to the inner three marker elements 24, thereby resulting in nine individual marker lines 26 in FIG. 6c and eight individual marker lines 26 in FIG. 6d.

The arrangement of marker elements according to FIG. 6e substantially corresponds to the arrangement of FIG. 6a, with the exception that the markers are spread over the entire area of compression element 8a, whereas in FIG. 6a marker elements 24 are only spread over the object distal region 22. It is to be noted that in both arrangements, according to FIGS. 6a and e, marker elements 24 arranged so as to not interfere with a tissue projection of object 10.

Figure 7:
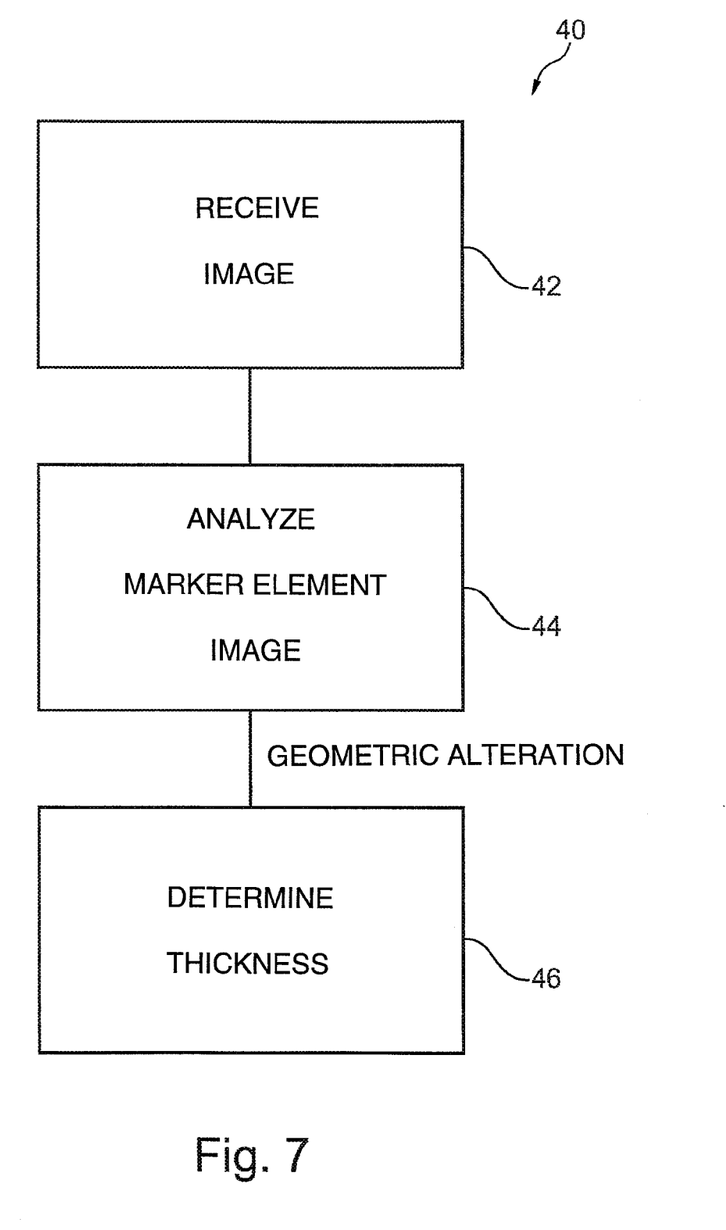
FIG. 7 shows an exemplary embodiment of a method for determining a deflection of a compression element.

Now taking reference to FIG. 7, a method of determining a deflection of a compression element is depicted.

Method 40 comprises receiving 42 image information of an object being compressed between a first compression element and a second compression element while performing image acquisition, wherein the image information comprises image information of at least one marker element; and determining 44 a geometrical alteration of the at least one compression element by analyzing the marker element image information in the received image information. Further, from the geometrical alteration of at least one compression element, a thickness of the object compressed between the first compression element and the second compression element may be determined 46, in particular for an object density assessment.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An X-ray imaging system element for determining a geometrical parameter of an object, comprising
   a first flexible, x-radiation penetrable compression element; and
   a second compression element;
   wherein the first compression element and the second compression element are:
   movable relative to one another and
   configured to receive a compressible object asymmetrically therebetween to define an object proximal region comprising the object and an object distal region not comprising the object;
   wherein the first flexible compression element is configured to flex altering its geometrical shape when the object is compressed between the first compression element and the second compression element;
   a plurality of partly X-ray opaque marker elements disposed on the first flexible compression element, the opaque marker elements being disposed in a plurality of non-parallel lines, each line including at least three marker elements;
   wherein the marker elements are arranged in the object distal region.

2. The system element according to claim 1, wherein the first flexible compression element is flexible in two dimensions and wherein the plurality of lines includes a plurality of the lines extending orthogonal to each other.

3. The system element according to claim 1, wherein the first flexible compression element is flexible in two dimensions and wherein the plurality of the lines includes at least a first plurality of the lines extending obliquely relative to a second plurality of the lines.

4. The system element according to claim 1, wherein the first flexible compression element is bendable in two dimensions and wherein each of the marker elements is shared by at least two lines.

5. The system element according to claim 1, comprising at least seven marker elements arranged in at least three non-identical marker lines.

6. The system element according to claim 4, comprising one of a combination of:
   seven marker elements and five non-identical marker lines;
   eight marker elements and six non-identical marker lines;
   nine marker elements and eight non-identical marker lines; and
   nine marker elements and nine non-identical marker lines.

7. The system element according to claim 1, wherein the marker elements include lead marker elements.

8. The system element according to claim 1, wherein the marker elements are circularly or spherically shaped.

9. The system element according to claim 1, wherein an alteration in a pattern of the lines is indicative of an alteration of the geometrical shape of the first compression element.

10. An X-ray imaging system comprising:
    an x-ray source;
    an x-ray detector; and the system element according to claim 1 disposed between the x-ray source and the detector.

11. A method for determining a geometrical parameter of a compressible object, the method comprising:

disposing the object between first and second compression elements, at least one of the compression elements being flexible and x-radiation penetrable, the flexible and x-radiation penetrable compression element including a plurality of lines, each line defined by at least three x-ray opaque marker elements, at least some of the lines being non-parallel to each other and sharing a marker element with at least one other line;

with an x-ray source, projecting x-radiation through the first and second compression elements and the object;

with a radiation detector, detecting the x-radiation which has passed through the first and second compression elements and the object to generate an x-ray image of the object and the markers;

based on differences between the lines on the flexible x-radiation penetrable compression element and the lines of markers in the x-ray image, assessing an object density.

12. An x-ray imaging system comprising:

a pair of compression elements configured to receive a compressible object between proximal ends of the compression elements, at least one of the compressible elements being flexible to bend in two dimensions and carrying a plurality of lines of x-ray opaque markers, each line of x-ray opaque markers including at least three markers with some of the markers being shared between two or more lines;

an x-ray source and an x-ray detector, the x-ray source and x-ray detector being disposed on opposite sides of the pair of compression elements and configured to project x-rays through the pair of compression elements and an object received therebetween and to detect x-rays which passed through the pair of compression elements and received object;

an actuator configured to apply a force to a distal end of the at least one flexible compression element to cause the at least one flexible compression element to bend and compress the object; and a processor configured to:

reconstruct radiation received by the radiation detector into an x-ray image of the lines of radiation opaque markers and object received between the proximal end of the compression elements; and based on an alteration of the lines of radiation opaque markers in the x-ray image when the force is applied, the object is compressed, and the at least one flexible compression element bends, determine a density of the compressed object.

* * * * *